(12) United States Patent
Hu

(10) Patent No.: US 9,184,204 B2
(45) Date of Patent: Nov. 10, 2015

(54) MULTI-SPECTRUM PHOTOSENSITIVE DEVICE

(75) Inventor: Xiaoping Hu, Shenzhen (CN)

(73) Assignee: BOLY MEDIA COMMUNICATIONS (SHENZHEN) CO., LTD., Shenzhen (CN)

( * ) Notice: Subject to any disclaimer, the term of this patent is extended or adjusted under 35 U.S.C. 154(b) by 318 days.

(21) Appl. No.: 13/699,534

(22) PCT Filed: Jun. 1, 2010

(86) PCT No.: PCT/CN2010/073440
§ 371 (c)(1),
(2), (4) Date: Nov. 21, 2012

(87) PCT Pub. No.: WO2011/150551
PCT Pub. Date: Dec. 8, 2011

(65) Prior Publication Data
US 2013/0062506 A1    Mar. 14, 2013

(51) Int. Cl.
*G01J 3/50* (2006.01)
*H01L 27/146* (2006.01)
(Continued)

(52) U.S. Cl.
CPC ............ *H01L 27/14647* (2013.01); *G01J 1/42* (2013.01); *G01N 21/6452* (2013.01);
(Continued)

(58) Field of Classification Search
CPC ............... H01L 27/14641; H01L 27/14647; H01L 27/14649; H01L 31/0352; G01J 1/42; G01N 21/6452; G01N 21/6454
USPC ........ 250/208.1, 226; 257/348, 290, 292, 299
See application file for complete search history.

(56) References Cited

U.S. PATENT DOCUMENTS 3,812,518 A * 5/1974 Kurz et al. ............... 257/465
5,751,049 A    5/1998 Goodwin
(Continued)

FOREIGN PATENT DOCUMENTS

CN    101345248 A    1/2009
CN    101577287 A    11/2009
(Continued)

OTHER PUBLICATIONS

International Search Report issued Mar. 24, 2011 in corresponding Application No. PCT/CN2010/073440.
(Continued)

*Primary Examiner* — Georgia Y Epps
*Assistant Examiner* — Kevin Wyatt
(74) *Attorney, Agent, or Firm* — Knobbe Martens Olson & Bear LLP

(57) ABSTRACT

A multi-spectrum photosensitive device comprises two, three, or four composite sensing pixels arranged in layers up and down in a base layer of P-type or N-type silicon by means of single-sided processing or double-sided processing, each composite sensing pixels can sense respectively spectrum orthogonal or complementary to each other in visible light or visible and infrared light. The basic sensing pixels on different layers of the composite sensing pixels can be designed to sense different colors or spectrums, so that a multi-spectrum photosensitive chip can be achieved by repeatedly arranging the macro units consisting of more than one composite sensing pixel. The present disclosure also includes a new multi-layer sensing pixel, and examples of which used in a single-sided double-layer, or a double-sided double-layer, or a double-sided three-layer, or a double-sided four-layer, or a single-sided mixed double-layer, or a double-sided mixed with double-layer or a multi-layer multi-spectrum sensing device. A multi-spectrum photosensitive device according to the present disclosure has the advantage of better color sensing performance, integration of color sensing and infrared sensing, and a simple processing technique.

26 Claims, 24 Drawing Sheets

(51) Int. Cl.
    *G01N 21/64* (2006.01)
    *G01J 1/42* (2006.01)
    *H01L 31/0352* (2006.01)

(52) U.S. Cl.
    CPC ....... *G01N 21/6454* (2013.01); *H01L 27/1464* (2013.01); *H01L 27/14641* (2013.01); *H01L 27/14649* (2013.01); *H01L 27/14652* (2013.01); *H01L 31/0352* (2013.01)

(56) References Cited

U.S. PATENT DOCUMENTS

| | | | |
|---|---|---|---|
| 7,868,367 B2* | 1/2011 | Hong et al. | 257/292 |
| 8,415,725 B2* | 4/2013 | Hirota | 257/291 |
| 2003/0020965 A1 | 1/2003 | LaRocca et al. | |
| 2004/0185597 A1* | 9/2004 | Merrill et al. | 438/70 |
| 2005/0139833 A1* | 6/2005 | Janesick et al. | 257/69 |
| 2007/0218578 A1 | 9/2007 | Lee et al. | |
| 2008/0217724 A1* | 9/2008 | Uya | 257/460 |
| 2010/0109060 A1 | 5/2010 | Mao et al. | |
| 2011/0291103 A1* | 12/2011 | Mazzillo | 257/76 |
| 2012/0193690 A1* | 8/2012 | Inoue et al. | 257/290 |
| 2013/0026342 A1* | 1/2013 | McCarten et al. | 250/208.1 |
| 2014/0183337 A1* | 7/2014 | Hu | 250/208.1 |
| 2014/0346356 A1* | 11/2014 | Giffard et al. | 250/338.4 |

FOREIGN PATENT DOCUMENTS

| | | |
|---|---|---|
| CN | 101640213 A | 2/2010 |
| CN | 101807590 A | 8/2010 |
| EP | 1903766 A2 | 3/2008 |
| JP | H02-177474 A | 7/1990 |
| JP | H07-245383 A | 9/1995 |
| JP | 2004-103964 A | 4/2004 |
| WO | WO 2009099493 A1 * | 8/2009 |

OTHER PUBLICATIONS

Knipp, Dietmar, et al., Vertically integrated amporphous silicon color sensor arrays, IEEE Transactions on Electron Devices, vol. 53, No. 7, Jul. 2006, pp. 1551-1557.

Extended European Search Report dated Jun. 27, 2013 in corresponding Application No. 10852350.7.

* cited by examiner

MULTI-SPECTRUM PHOTOSENSITIVE DEVICE

CROSS-REFERENCE TO RELATED APPLICATIONS

This application is the U.S. National Phase under 35. U.S.C. §371 of International Application PCT/CN2010/073440, filed Jun. 1, 2010. The disclosures of the above-described application are hereby incorporated by reference in their entirety. The International Application was published under PCT Article 21(2) in a language other than English.

TECHNICAL FIELD

The present disclosure relates to a multi-spectrum photosensitive device, in particular, to physical implementation and manufacture thereof. More particularly, the present invention relates to a sensing device for panchromatic images which is achievable by CCD or CMOS semiconductor for simultaneously sensing several spectra (such as visible light and infrared). Herein, the panchromatic spectrum (or color) comprises the entire spectra of interest. For normal sensing devices (e.g., those for visible light), the panchromatic refers to the entire spectra of visible light that contains red, green, blue and white. For sensing devices used for a combination of infrared and visible light, the panchromatic refers to spectra of the visible light and infrared. The present disclosure applies to multi-spectrum sensing device for sensing infrared, monochrome and color images.

BACKGROUND ART

The present disclosure is a continuation of earlier applications titled "Multi-spectrum Photosensitive Device and Manufacturing Methods Thereof" (PCT/CN2007/071262) and "Multi-spectrum Photosensitive Device and Manufacturing Method Thereof" (Chinese Application No. 200810217270.2) owned by the present inventor, and aims to provide more specific and preferred semiconductor physical implementations.

The previous sensing devices focus on sensing either color visible light or infrared light, few of them sense both of color visible light and infrared light. Although there are other inventions or applications, such as using indium antimony semiconductor technology ("Silicon infrared focal plane arrays", M. Kimata, in Handbook of Infrared Detection Technologies, edited by M. Henini and M. Razeghi, pp. 352-392, Elsevier Science Ltd., 2002), to simultaneously realize photosensitivity of visible light and infrared light, they do not sense color of light. The existing method of simultaneously obtaining the color and infrared light is to physically superpose a color sensing device with an infrared sensing device (such as "Backside-hybrid Photo detector for trans-chip detection of NIR light", by T. Tokudaetal, in IEEE Workshop on Charge-coupled Devices & Advanced Image Sensors, Elmau, Germany, May 2003, and "A CMOS image sensor with eye-safe detection function using backside carrier injection", T. Tokudaetal, J. Inst. Image Information & Television Eng., 60(3):366-372, March 2006).

There are three main reasons for failure of the existing sensing device in integrating the color sensing device with infrared sensing device. The first reason is that the existing color sensing device needs to use color filter film (including red/green/blue, or cyan/yellow/magenta/green) to get the color. However, these filter films also have a strong filtering characteristic on the infrared light. In addition, in order to make color vivid, an infrared filter is added to the lens specifically to reduce the possible fogging phenomenon caused by infrared light on color image. Foveon Company's X3 three-layer sensing technology achieves the selection of color according to the depth. Though this method does not use the filter film, the manufacture of the three-layer sensing technology has been very difficult and industrialization is not very successful. If an infrared layer is further added below the three layers, it will be more complicated and there is almost no practical value. The second reason is that silicon that is widely used in semiconductors absorbs the infrared with wavelength only below 1100 nm. Therefore, many infrared sensing devices utilize other semiconductor materials, such as germanium, silicon-germanium mixed crystals, HgCdTe, InSb and the like. These materials are not suitable for sensing visible light. The third reason is due to lack of practicable technology for manufacturing double-layer or multi-layer sensing device.

Therefore, some problems, such as how to achieve better photosensitivity and integrate the color sensing device with infrared sensing device, needs to be further invented and improved.

SUMMARY

Technical Problem

Based on the above description, the present disclosure provides a multi-spectrum sensing device, which not only achieves color photosensitivity better, but also provides an implementation for integrating a color sensing device with an infrared sensing device.

Technical Solution

The technical solution according to the present invention includes:

A multi-spectrum photosensitive device, comprising a base layer, wherein a plurality of composite sensing pixel macro units is repeatedly arranged in accordance with a preset pattern on the base layer, the composite sensing pixel macro unit comprises at least one composite sensing pixel comprising at least two basic sensing pixels, the basic sensing pixels are arranged in layers along a direction of light irradiation, each layer having one basic sensing pixel, and the basic sensing pixels are distributed at the top side, or bottom side, or top side and bottom side of the base layer in a manner of each side with at most two layers.

In an example of the multi-spectrum photosensitive device, the composite sensing pixel includes two basic sensing pixels, which are arranged in two layers at the top side or bottom side of the base layer to form a single-side double-layer composite sensing pixel, or are disposed respectively at the top side and bottom side of the base layer to form a double-sided double-layer composite sensing pixel.

In the multi-spectrum photosensitive device, the composite sensing pixel in the base layer may be a single-sided double-layer composite sensing pixel, so that the multi-spectrum sensing device constitutes a single-sided double-layer sensing device.

The single-sided double-layer composite sensing pixel may be formed by a composite N-P-N junction which is formed by doping P-type impurity on a base layer of N-type silicon to make a P-doped layer, then doping N-type impurity on P-doped layer.

The single-sided double-layer composite sensing pixel could be formed by a composite P-N-P junction, which is formed by doping N-type impurity on a base layer of P-type silicon to make an N-doped layer, then doping P-type impurity on the N-doped layer.

In the multi-spectrum photosensitive device, the composite sensing pixel in the base layer may be a double-sided double-layer composite sensing pixel, so that the multi-spectrum sensing device constitutes a double-sided double-layer sensing device.

The double-sided double-layer composite sensing pixel may be formed by a composite P-N-P junction which is formed by doping P-type impurity on both top side and bottom side of a base layer of N-type silicon.

The double-sided double-layer composite sensing pixel may be formed by a composite N-P-N junction which is obtained by doping N-type impurity on both top side and bottom side of a base layer of P-type silicon.

In an example of the multi-spectrum photosensitive device, the composite sensing pixel includes three or four basic sensing pixels, two of which are disposed in two layers at top side or bottom side of the base layer, and the remain basic sensing pixel(s) are disposed in one or two layers at bottom side or top side of the base layer, so as to form a double-sided multi-layer composite sensing pixel.

In the multi-spectrum photosensitive device, a composite sensing pixel in the base layer may be a double-sided multi-layer composite sensing pixel, so that the multi-spectrum sensing device constitutes a double-sided multi-layer sensing device.

The double-sided multi-layer composite sensing pixel may be formed by a composite junction of P-N-P, or N-P-N-P, or P-N-P-N, or N-P-N-P-N, wherein the composite junction is made by doping P-type impurity on both top side and bottom side of a base layer of N-type silicon to make a P-doped layer, and then doping N-type impurity on the P-doped layer.

The double-sided multi-layer composite sensing pixel may be formed by a composite junction of N-P-N, N-P-N-P, P-N-P-N or P-N-P-N-P, wherein the composite junction is made by doping N-type impurity on both top side and bottom side of a base layer of P-type silicon to make an N-doped layer, and then doping P-type impurity on the N-doped layer.

In the multi-spectrum photosensitive device, the basic sensing pixels in the composite sensing pixel respectively senses one of two spectrum bands of visible light or visible and infrared light orthogonal to each other, the combination of spectra sensed by all the composite sensing pixels in the composite sensing pixels macro units contains spectral information indispensable for color reconstruction within the color space of RGB or CMYK.

In the multi-spectrum photosensitive device, the spectrum sensed by the basic sensing pixels of the composite sensing pixels closest to the light source includes blank color, blue, green, cyan, white, and white plus infrared.

In the multi-spectrum photosensitive device, the spectrum sensed by basic sensing pixels of the composite sensing pixels farthest away from the light source includes blank color, green, red, yellow, white, red plus infrared, yellow plus infrared, and white plus infrared.

In the multi-spectrum photosensitive device, the bottom surface of the basic sensing pixel sensing infrared light in the bottom layer of the composite sensing pixel units is grown with silicon germanium crystal layer or germanium crystal layer for absorbing infrared light better.

In the multi-spectrum photosensitive device, the bottom of the basic sensing pixels for sensing infrared light is coated with a mirror reflection film.

In the multi-spectrum photosensitive device, the composite sensing pixel is sampled in an active manner to form an active pixel.

In the multi-spectrum photosensitive device, the composite sensing pixel is sampled in a passive manner to form a passive pixel.

In the multi-spectrum photosensitive device, the basic sensing pixel in the composite sensing pixels is a photo diode or a photo gate.

In the multi-spectrum photosensitive device, sensing mode of the multi-spectrum sensing device comprises front side sensing, back side sensing, or double-direction sensing mode, the double-direction sensing mode includes direction-selected-by-time-sharing mode, direction-selected-by-area-division mode, or direction-selected-by-pixel mode.

In the multi-spectrum photosensitive device, the preset pattern includes repeated ordering, rectangular pattern, or honeycomb pattern adopted by the composite pixels.

Beneficial Effect

The beneficial technical effects of the present disclosure are designed to:

1. A better color sensing performance is provided and a color sensing device is integrated with an infrared sensing device. In the present disclosure, at least two sensing pixel layers are provided in a direction of the light source irradiation in the form of composite sensing pixel containing at least two basic sensing pixels, the basic sensing pixels senses each spectral band of the spectrum at various layers, so that it is implemented that at least two spectral bands can be sensed at the same pixel position of one surface of the base layer but at different depths, so as to provide a better flexibility and a more pixel disposition on pattern arrangement of composite sensing pixel macro unit of the surface thereon, so that the sensibility, resolution and dynamic scope of the sensing device are greatly enhanced. On the other hand, when two sensing pixel layers are disposed as one sensing visible light and the other sensing infrared light, the integration of visible light device and infrared light device is realizable easily to sense color light and infrared light simultaneously.

2. The processing technique implementing products is simple. By adopting existing CCD or CMOS sensing chip processing techniques and equipment, the present disclosure could easily manufacture a single-sided double-layer multi-spectrum sensing device, double-sided double-layer multi-spectrum sensing device and double-sided multi-spectrum sensing device for front side sensing, back side sensing or double-direction sensing. For the Foveon company's three-layer sensing device mentioned above, in order to carry out color sensing, it is necessary to dispose three layers at the same position to respectively sense three RGB colors so as to carry out color reconstruction. However, such method is difficult in processing three layers, and obviously makes wiring between transistors difficult, since connectors for different layers need to be separated from each other. Based on that, it is almost impossible for adding one more layer to the three RGB layers to perform infrared sensing. While the present disclosure carries out color reconstruction with pixel arranged in a pattern on the surface, so that it is unnecessary to dispose three layers in the direction of depth to implement color reconstruction, hence better color sensing performance is realized in the manner of dispose only two layers of basic sensing pixels on the same one surface. Since only two sensing pixel layers at most are disposed on the same surface, the difficulty of three-dimensional processing techniques is distinctly decreased, and wiring is relatively easy. Especially when a double-sided double-layer method is utilized, i.e. two basic sensing pixels in the composite sensing pixels are respectively disposed on two opposite sides, not only the single side double-layer method has better color sensing performance, but also each side processing is simplified as planar processing, that is, one sensing pixel layer is plane-processed on one side, then the base layer is turned over and the other sensing pixel layer is again plane-processed, so that the processing technique of double-sided double-layer sensing device is similar to that of current single-sided single-layer sensing device.

3. Because the sensing device of the present disclosure carries out color reconstruction by combining depth spectrum filter and plane pattern arrangement, on one hand, it is unnecessary to adopt a color film, which greatly enhances production yield. On the other hand, redundant color information may be obtained so that many bad spots and dead spots could be compensated by background processing and the use of redundant color information. Accordingly, the fault occurrence ratio of the sensing device is decreased overall.

A plurality of the double-layer and multi-layer multi-spectrum sensing device suitable for sensing visible and infrared light according to embodiments of the present disclosure will be discussed, which are exemplary only for demonstrating the present disclosure, and are not intended to limit the protection scope of the present disclosure.

For those skilled in the art, the above and other purposes as well as advantages of the present disclosure will be apparent from the detailed description and illustration of preferred embodiments with reference to the drawings as shown below.

For the sake of simplicity, the following descriptions of drawings are mainly based on photo diode. However, almost all the examples may also use photo gate instead.

DESCRIPTIONS OF THE DRAWINGS

FIG. 1 is a schematic diagram of traditional single-layer photo diode.

FIG. 2 is a schematic diagram of a three-layer composite photo diode invented by Foveon Company, in which the diode at top layer senses blue, the diode at middle layer senses green, and the diode at bottom layer senses red. This manner makes full use of the relationship between light penetration depth and wavelength. From this figure we can imagine the difficulties of such kind of sensing device on pixel reading, for example, for the pixels of three distinct colors, the reading circuit will occupy a large space and the wiring will be difficult.

FIG. 3 (a) and FIG. 3 (b) are schematic diagrams of double-layer multi-spectrum sensing devices according to the present disclosure respectively. FIG. 3(a) is suitable for illustrating a single-sided double-layer sensing device, and FIG. 3(b) is suitable for illustrating a double-sided double-layer sensing device. The depths of $T_1$, $T_2$, $T_3$, and $T_4$ are determined in accordance with the relationship curve between incident depth and wavelength of light in the base material (silicon) (Gerald C. Hoist and Terrance S. Lomheim, "CMOS/CCD Sensors and Camera Systems", JCD Publishing, pp. 125-125, ISBN 9780819467300, 2007). For example, if the photo diode at top layer is intended to sense blue (or cyan), $T_1$ should be chosen as about 1.5 um (or about 4.5 um); and if the bottom layer is intended to obtain red, $T_2$ and $T_4$ should be at least 8 um, and $T_3$ should be at least 4.5 um. If the photo diode at bottom layer is intended to obtain blue yellow, $T_2$ and $T_4$ should be at least 8 um, and $T_3$ should be at least 1.5 um. The photo diode at top layer and the bottom layer form a composite diode pair (composite sensing pixels). When the light is irradiated from the top, the photo diode at top layer is closer to the light source. When the light is irradiated from the bottom, the photo diode at bottom layer is closer to the light source.

FIG. 4 (a) and FIG. 4 (b) show a composite photo diode pair (composite sensing pixels) for sensing both the visible light and the infrared light simultaneously. In order to receive infrared light, the thickness of silicon substrate (T2 and T4 in FIG. 3) can be thicker.

FIG. 5 (a) and FIG. 5 (b) are the situation of the composite photo diode pair in a single-layer sensing device being irradiated from the back side, in which the photo diode in FIG. 5 (a) only senses visible light, and the photo diode in FIG. 5 (b) senses both visible light and infrared light. In order to make the two composite photo diodes have a basically same thickness, germanium or silicon germanium crystal (SiGe), which can absorb infrared light better, can be grown at the back of the photo diode sensing the infrared light.

FIG. 6 (a) and FIG. 6 (b) are the situation of composite photo diode pair in a double-sided double-layer sensing device being irradiated from the front side, in which the photo diode in FIG. 6 (a) only senses visible light, and the photo diode in FIG. 6 (b) senses both visible light and infrared light. Similarly, in order to make the two composite photo diodes have a basically same thickness, germanium or silicon germanium crystal (SiGe), which can absorb infrared light better, can be grown at the back of the photo diode sensing the infrared light.

FIG. 7 shows the situation of a composite photo diode in FIG. 3 (a) with reading means. Due to the difficulty of wiring and sharing reading circuit, the single-sided double-layer sensing device is more suitably implemented with passive pixel (without FD and amplifying circuit).

FIG. 8 shows the situation of composite photo diode in FIG. 3 (b) with reading means. In contrast, when disposing reading circuit, the double-sided double-layer sensing device is easier and more flexible than the single-layer sensing device. Therefore, the double-sided double-layer sensing device can be achieved by either passive pixel, or active pixel. Furthermore, if it is achieved by active pixel, each pixel can be read with using only an average of 1.5 gates (utilizing 3T reading circuit), or 1.75 gates (utilizing 4T reading circuit).

FIG. 9 shows a currently good reading circuit for a 4T active sensing pixel shared by 4-point, wherein one pixel utilizes 1.75 gates on average. We use it to explain that the double-layer or multi-layer sensing device according to the present disclosure could utilize the current standard reading and sampling circuit.

FIG. 10 shows an example of a double-sided three-layer sensing device obtained by simply and directly applying a single-sided double-layer sensing device to bidirectional sensing, wherein the front side in FIG. 10 (a) has one layer and the back side therein has two layers, while the front side in FIG. 10 (b) has two layers and the back side therein has one layer. Such a sensing device with also three layers is easier and has more variations than Foveon Company's X3 three-layer sensing device. Take note to the difference between FIG. 10 and FIG. 2. The sensing pixels sensing three colors in FIG. 2 are crowded on one side, while in FIG. 10, there are only two pixels on one side and another pixel on the other side.

FIG. 11 shows a double-sided four-layer sensing device generated by combining a single-sided double-layer sensing device and double-sided sensing mode. By using such a sensing device, four colors of blue, green, red and infrared may be sensed by one pixel. Although there are more colors and more layers, the manufacturing of the sensing device is much easier than that of Foveon Company's X3 three-layer sensing device.

Figure 15:
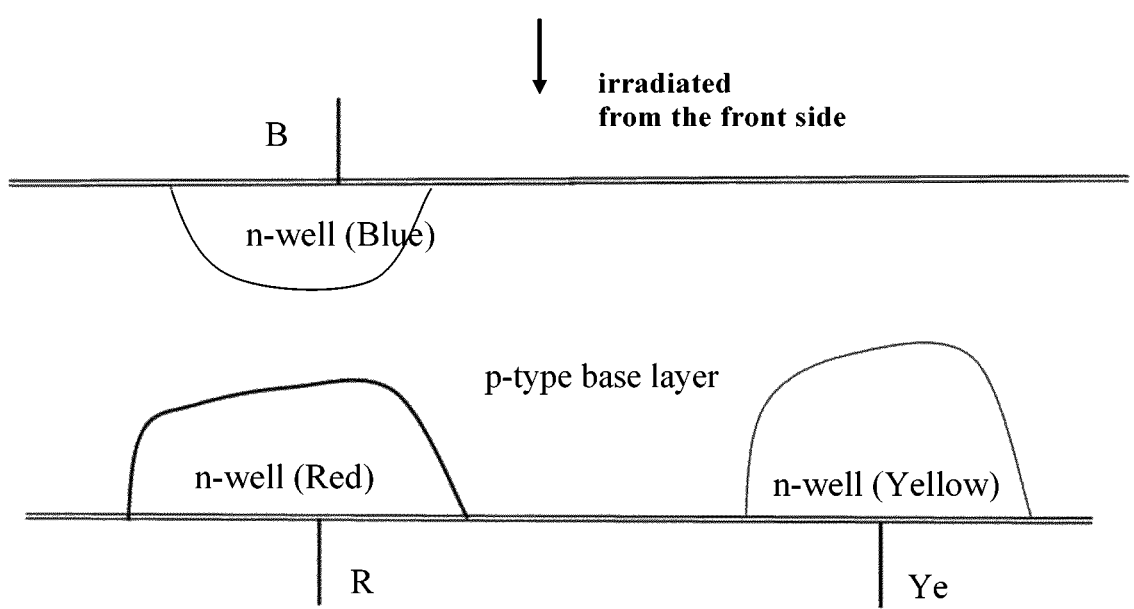
FIG. 15 and FIG. 16 show examples of single-sided or double-sided double-layer sensing device with mixing two layers and one layer.
Figure 16:
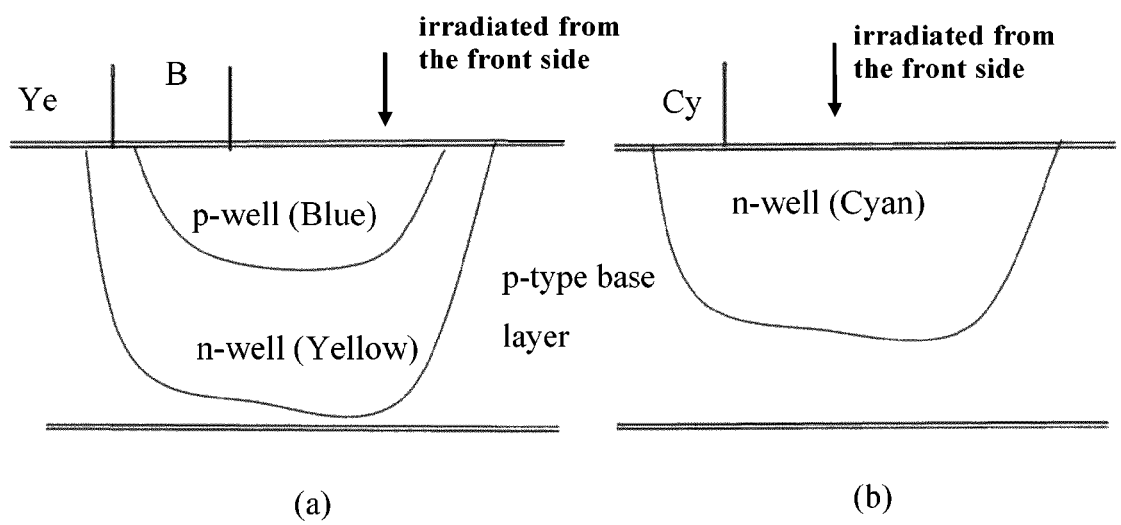

We see a degenerative case of a multi-layer composite sensing pixel in FIGS. 12-16: if one of the N-layer composite sensing pixels is a blank pixel, N-layer composite sensing pixels are degenerated to (N−1)-layer composite sensing pixels. Some double-layer sensing pixels degenerated to a single layer are shown in FIGS. 15 and 16. If two of the N-layer composite sensing pixels are blank pixels, N-layer composite sensing pixels are degenerated to (N−2)-layer composite sensing pixels, and so forth.

When the number of layers in the composite pixel is inconsistent, some of the layers may be treated as containing blank pixels (sensing blank color). Therefore, a mixed multi-layer sensing device is a specific case of a multi-layer sensing device, i.e. some of the composite pixels contain blank pixels.

These examples sufficiently demonstrate the capacity of a single-side double-layer sensing device and a double-sided double-layer or multi-layer sensing device. A series of new colorful sensing device with high performance is generated by combining the technologies of the two devices. It is specifically noted that, in a sensing device with more than three layers, the spectrum sensed by a photo diode positioned in each layer must be orthogonal to each other (that is, there is no common or overlapped portion, theoretically).

Figure 17A:
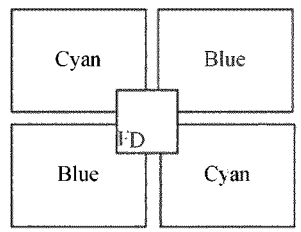
Figure 17B:
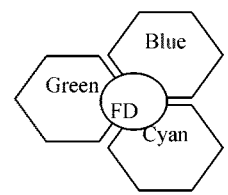

FIG. 17 (a) and FIG. 17 (b) shows a top view of a double-sided double-layer sensing device with rectangular pattern and honeycomb pattern, wherein FD is a reading capacitor shared by the upper layer and the lower layer. Of course, if needed, the upper layer and the lower layer could utilize a reading capacitor, respectively, even if using a group of reading capacitors, respectively.

Figure 9:
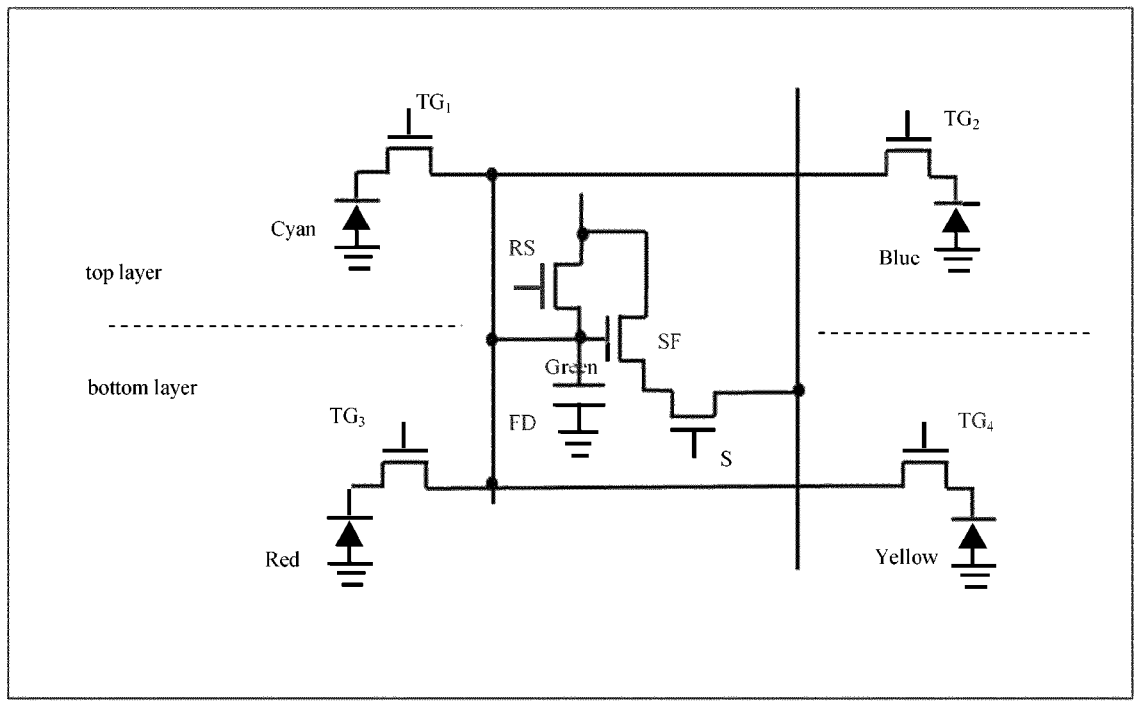
Figure 10:
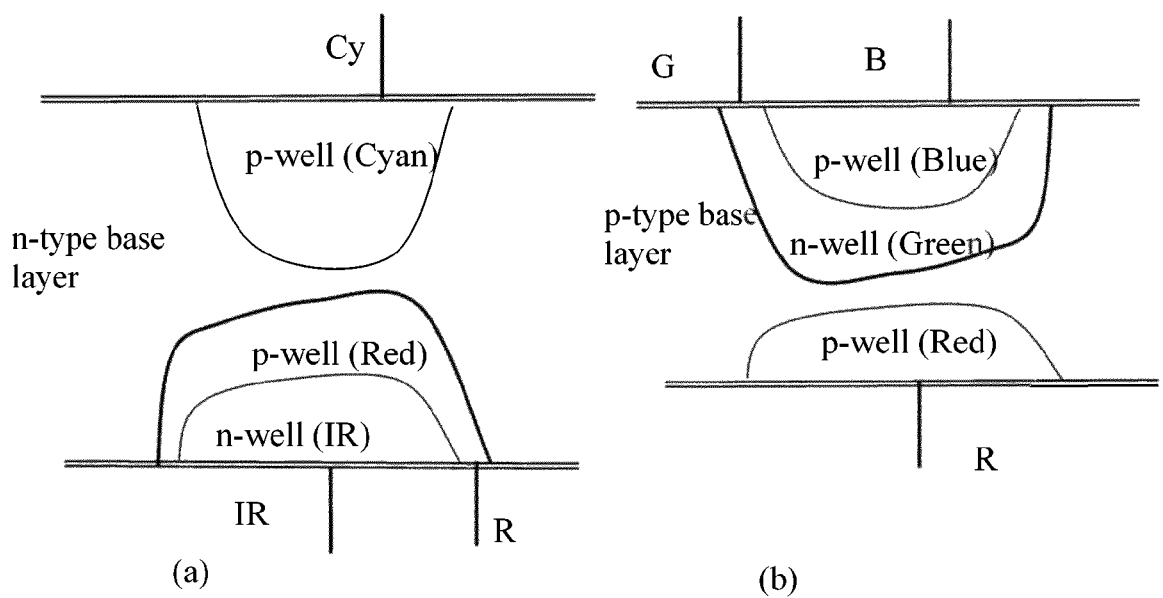
Figure 11:
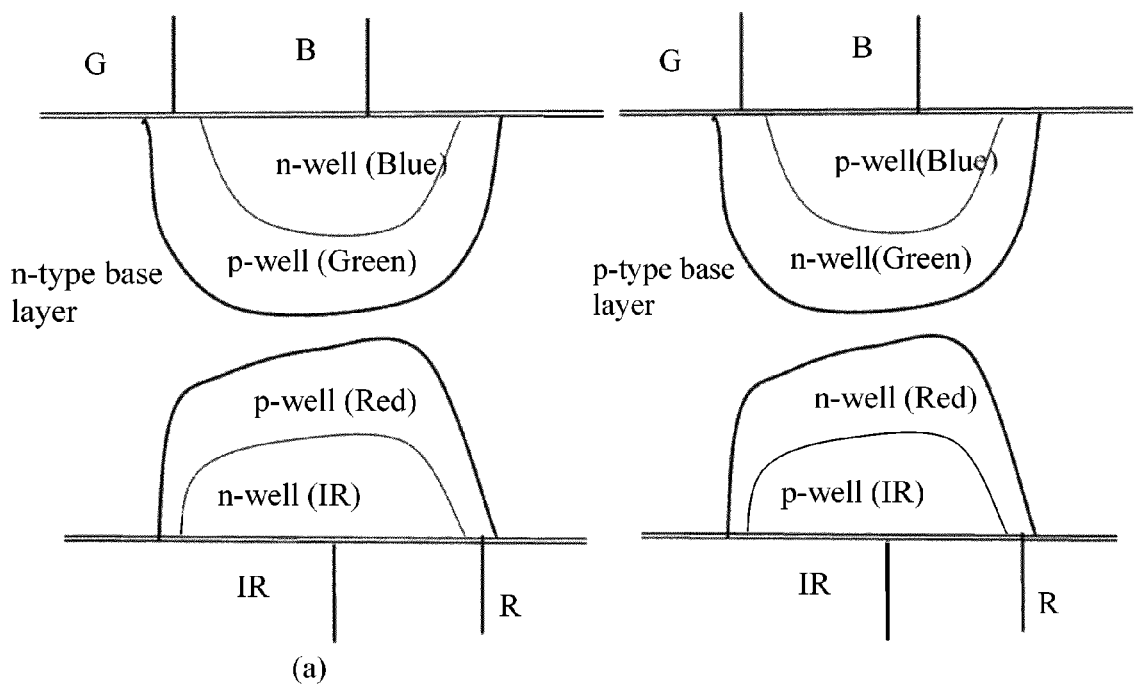
Figure 12:
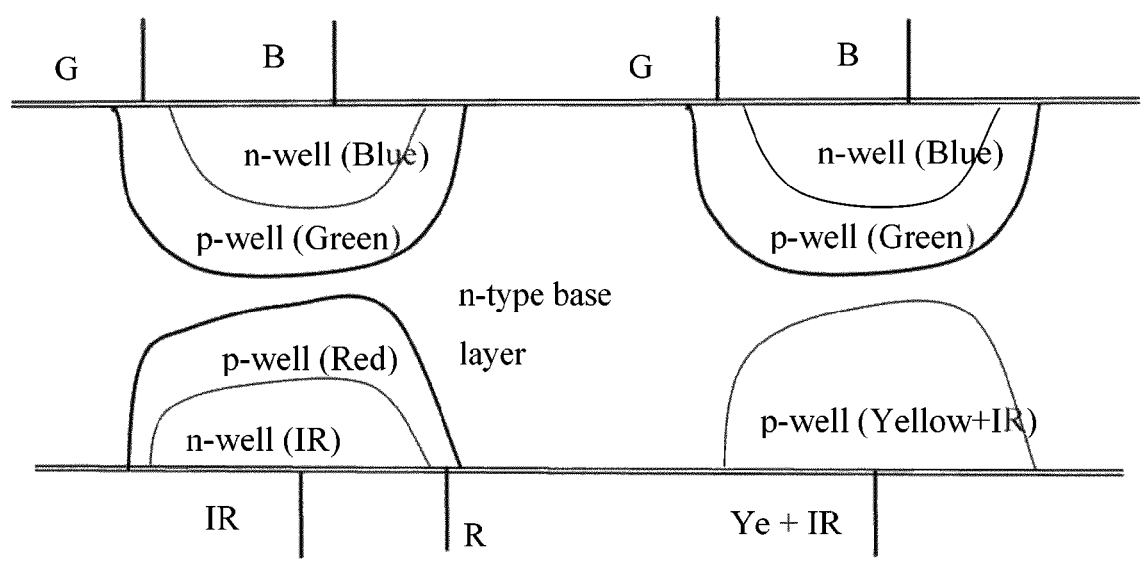
FIG. 12 shows examples of a double-sided multi-layer sensing device with mixing three layers and four layers.
Figure 13:
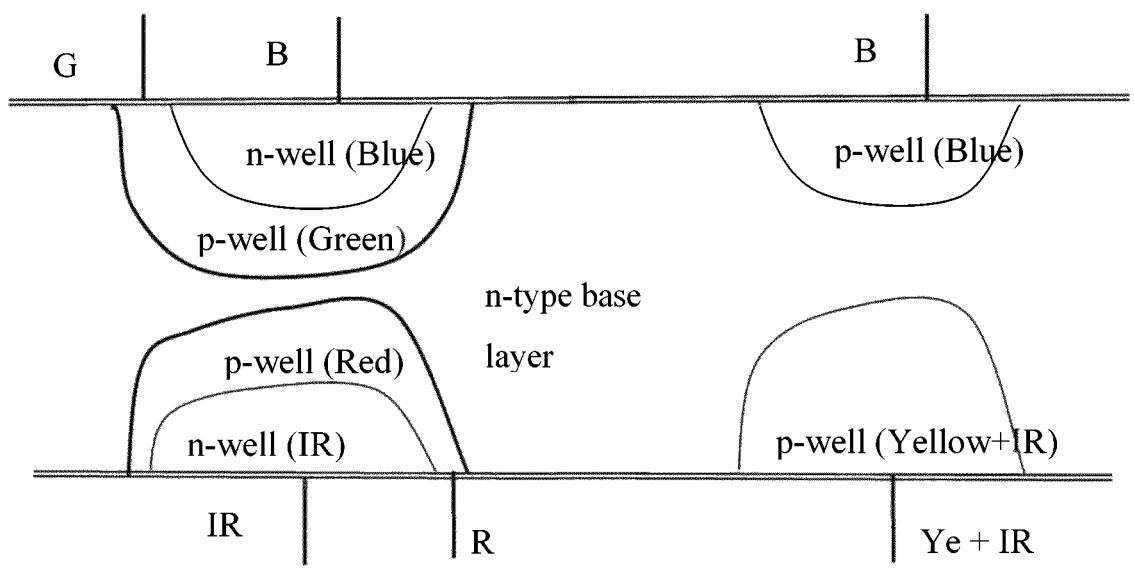
FIG. 13 shows examples of a double-sided multi-layer sensing device with mixing two layers and four layers.
Figure 14:
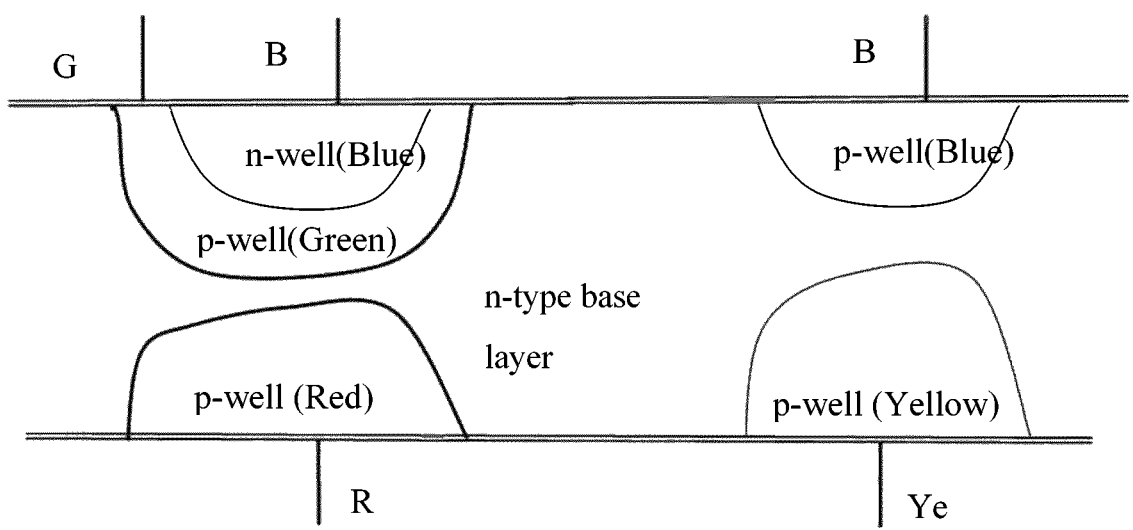
FIG. 14 shows examples of a double-sided multi-layer sensing device with mixing two layers and three layers.
Figure 18A:
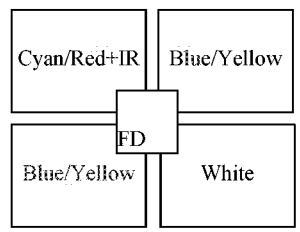
Figure 18B:
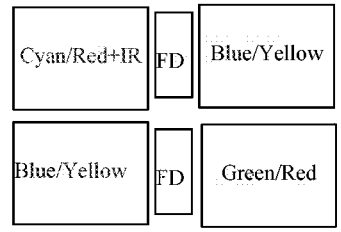

FIG. 18 (a) shows a top view of a double-sided double-layer multi-spectrum (sensing color plus infrared) sensing device with rectangular pattern, wherein FD is a reading capacitor shared by the upper layer and the lower layer. FIG. 18 (b) shows a top view of a double-sided double-layer multi-spectrum (sensing color plus infrared) sensing device with rectangular pattern, wherein FD is a reading capacitor sharing the upper layer and the lower layer. Such kind of macro-pixel unit consisted of two composite pixels could also utilize active sensing pixels with 4-point sharing reading circuit as shown in FIG. 9. Different from the single-side single-layer sensing device, the device in FIG. 18 (a) adopts four sensing diodes sharing a reading circuit disposed on two sides.

Figure 19:
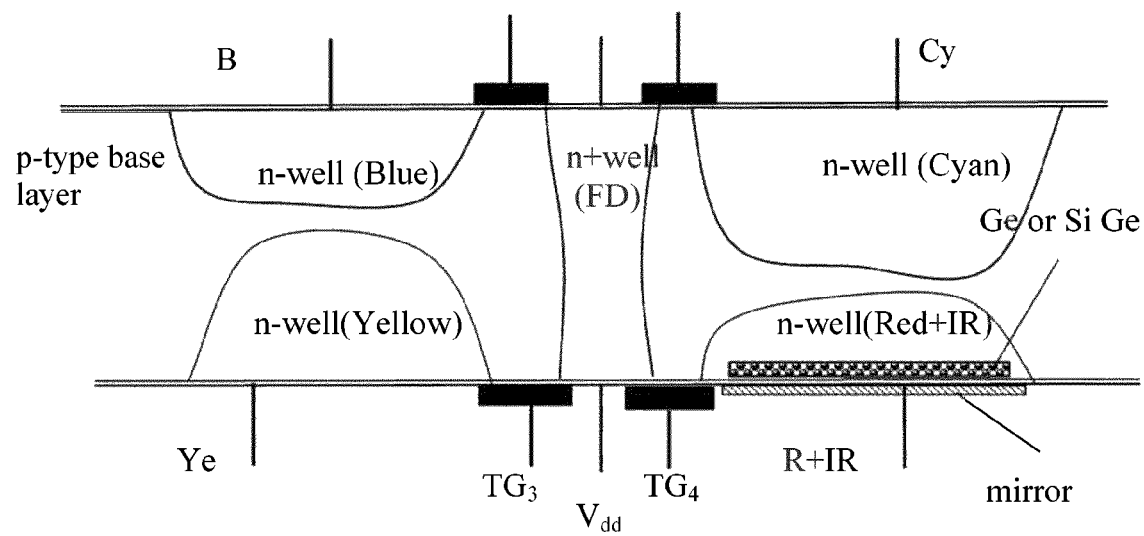

FIG. 19 shows a cross sectional view of 8-point or 4-point sharing reading circuit of a double-sided double-layer multi-spectrum (color plus infrared) sensing device (omitting 3T or 4T reading circuit). Here is an extreme case of FD which connects the upper layer and the lower layer. For a double-sided double-layer multi-spectrum (color plus infrared) sensing device, even if a 4-point sharing reading circuit also has two choices: one is that the 4 points are on the same surface, the other is that the 4 points are on different surfaces. In this diagram, we use another method to improve the absorbing efficiency of infrared light, i.e., mirror reflection materials (such as aluminum, silver or other reflection materials well matched with germanium or silicon) are coated at the back of the germanium layer and the silicon-germanium layer.

Figure 20:
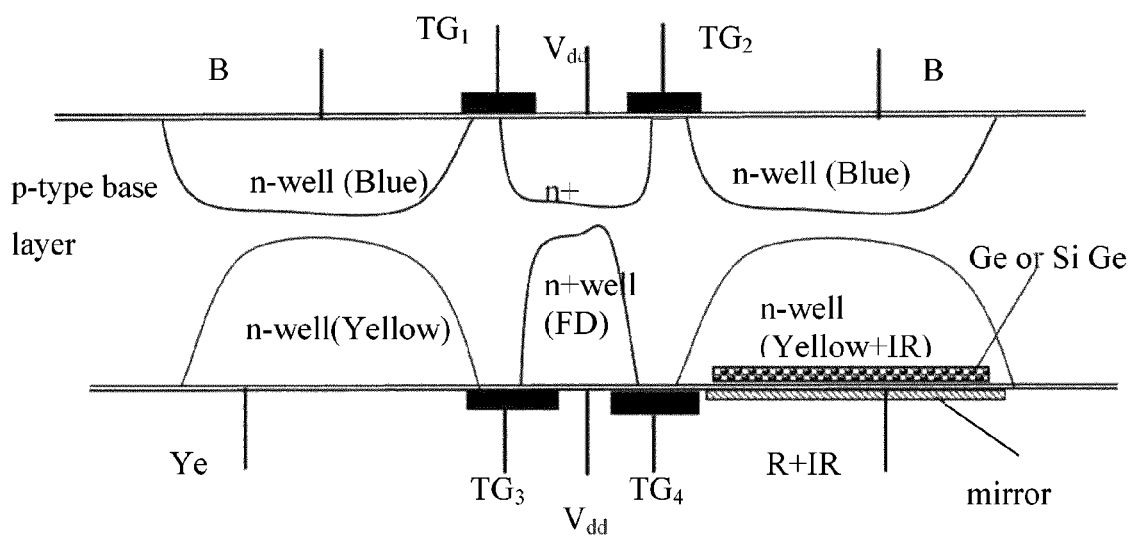

FIG. 20 shows a cross section view of an 8-point or 4-point sharing reading circuit of the double-sided double-layer multi-spectrum (color plus infrared) sensing device (omitting 3T or 4T reading circuit). Here is a simpler case of FD not connecting upper layer and lower layer. When FD is not connecting the upper layer and lower layer, the top side or the bottom side of the double-sided double-layer multi-spectrum sensing device is the same as that of the single-sided single-layer sensing device.

Figure 21:
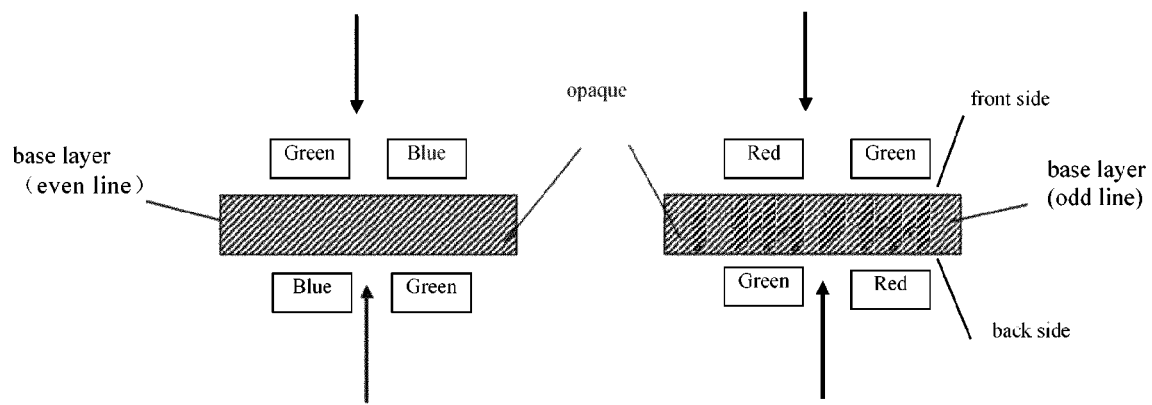

FIG. 21 shows a simple situation of producing the double-sided double-layer sensing device. When the base layer is opaque, the upper layer and lower layer can be achieved by a simple method of repeating the processing of the single-sided single-layer sensing device twice. The devices on both sides of the device can also be completely independent. This is a most simple method to achieve a double-direction sensing device.

FIG. 22 (a) and FIG. 22 (b) show a situation of a single-sided double-layer sensing devices being used for front side sensing and back side sensing, respectively. It is noted that, in the double-layer photo diode pairs, the photo diode closer to the light source will obtain color with shorter wavelength.

Figure 23:
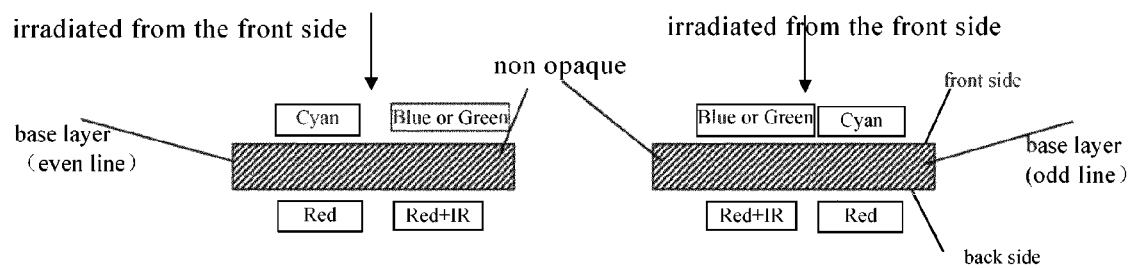
Figure 23:
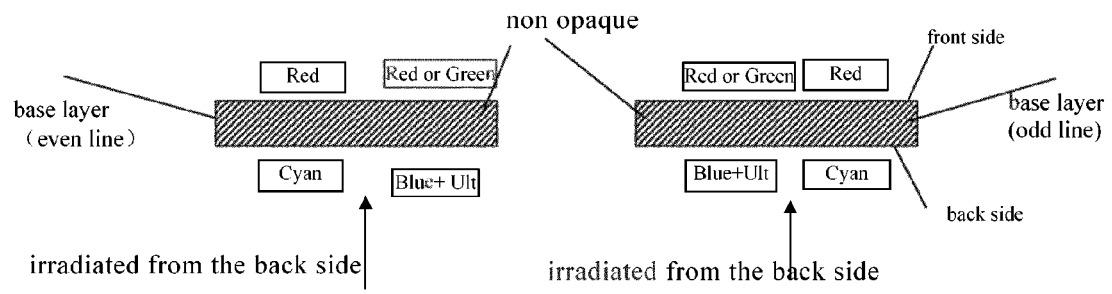

FIG. 23 (a) and FIG. 23 (b) show a situation of a double-sided double-layer sensing devices being used for front side sensing and back side sensing, respectively. It is noted that, when the direction of light source is changed, the color sensed by the double-layer photo diode pairs will changed, too. Generally, for two-way symmetrical double-sided double-layer sensing devices (referring to Chinese Application No. 200810217270.2, titled "Multi-spectrum sensing device and manufacturing method thereof"), when the direction of light source changes is changed, cyan and yellow will be exchanged, and blue and red will be exchanged, while green remains the same.

Figure 24:
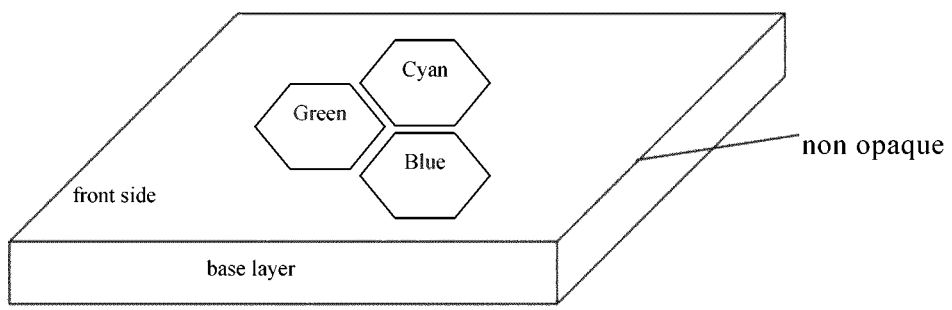
Figure 24:
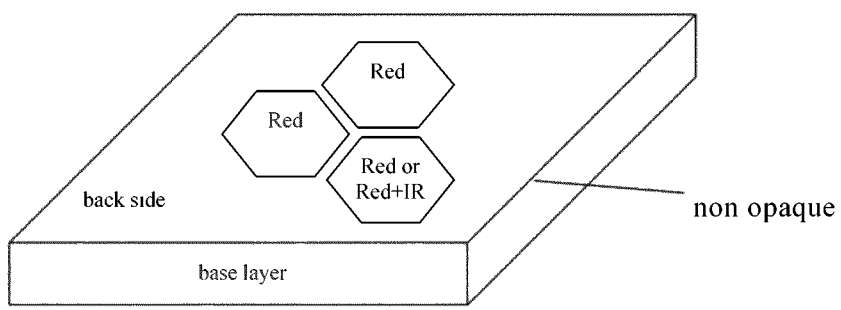

FIG. 24 (a) and FIG. 24 (b) show a situation of the front side and back side of a double-sided double-layer sensing device, in which macro pixel comprises three composite photo diodes (composite sensing pixels). When the macro pixel comprises three pixels, the three pixels are usually arranged in honeycomb pattern.

Figure 25:
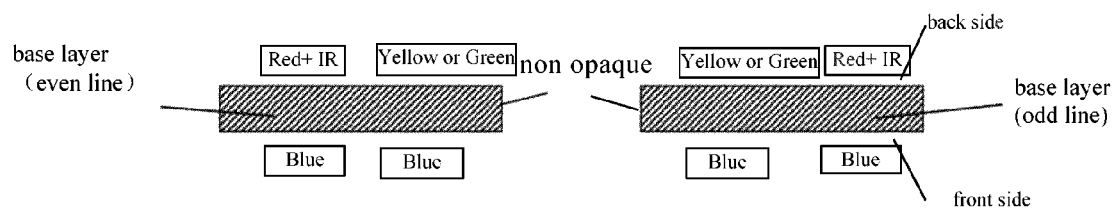
Figure 26:
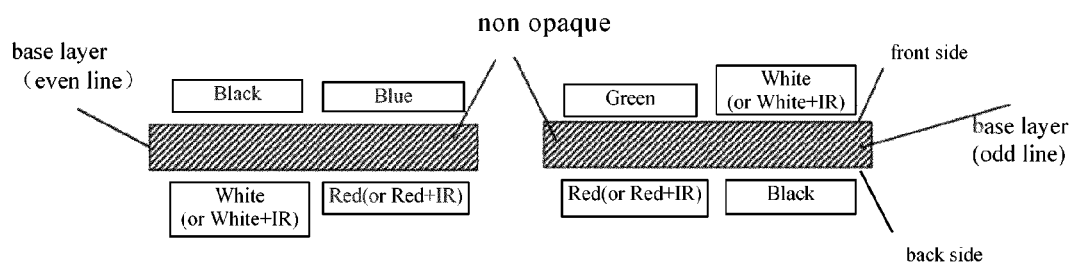
Figure 27:
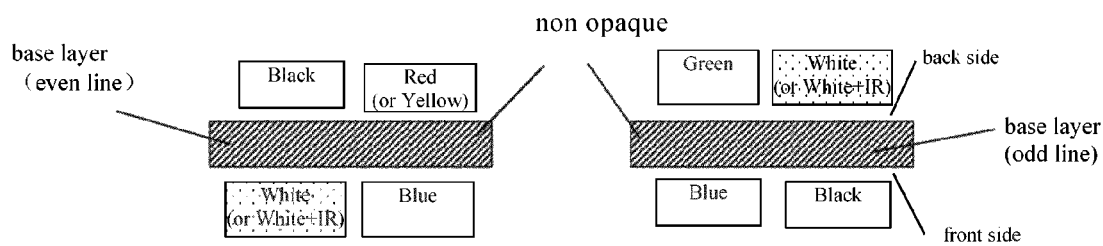

FIG. 25, FIG. 26, and FIG. 27 are other possible implementations of a double-sided double-layer sensing device. These figures fully show the features of flexibility and diversity of a double-sided double-layer device. After a reasonable change, the discussions with respect to composite diodes in FIGS. 3-16 are also applicable to the situation of FIGS. 22-27. The small numbers of figures are just used to illustrate the principle, rather than limiting the essence and scope of the present disclosure.

Figure 28:
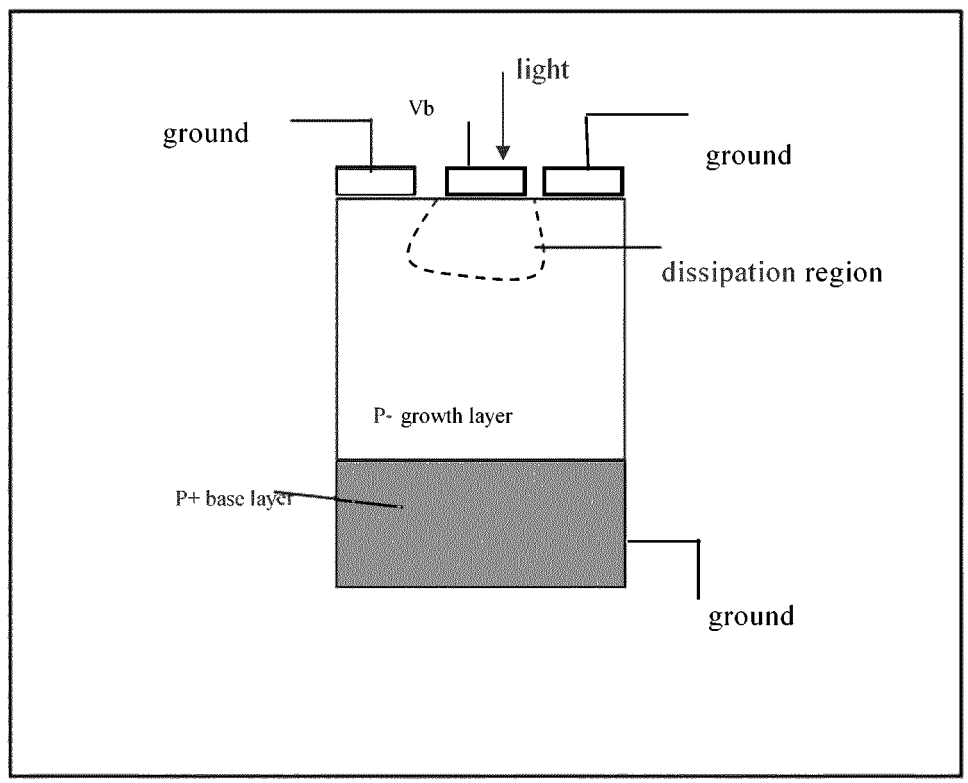

FIG. 28 is a principle schematic diagram of a photo gate. In the above illustration, if photo diode used as a basic sensing pixel is replaced by a photo gate, many completely similar implementations and conclusions can be obtained.

DETAILED DESCRIPTION

In order to facilitate describing the disclosure and explaining differences between the invention and existing technology, the following definition of the terms are provided: double-layer sensing device, multi-layer sensing device, double-sided sensing device, double-direction sensing device. The double-layer sensing device means that sensing pixels thereof are physically divided into two layers, each of which contains sensing pixels for sensing specific spectrum. The multi-layer sensing device refers to a sensing device with more than two layers, such as Foveon Company's X3 sensing device. The double-sided sensing device refers to a sensing device with two sensing surfaces, each of which can sense light from at least one direction. The bidirectional sensing device means that the sensing device can sense light from two directions (which usually form an angle of 180 degrees), i.e., both the front side and the back side of the sensing device can sense light.

Figure 22A:
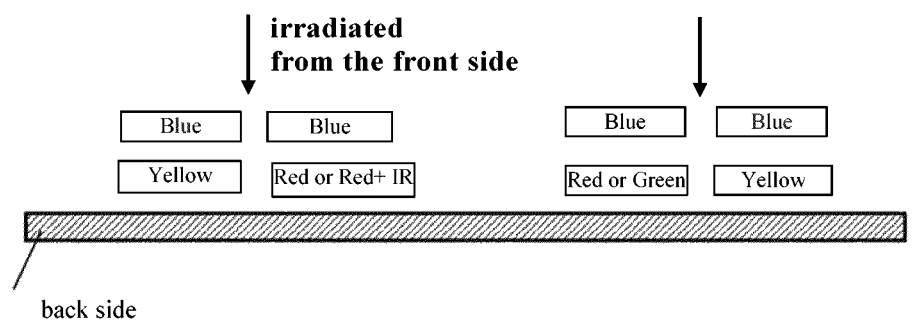
Figure 22B:
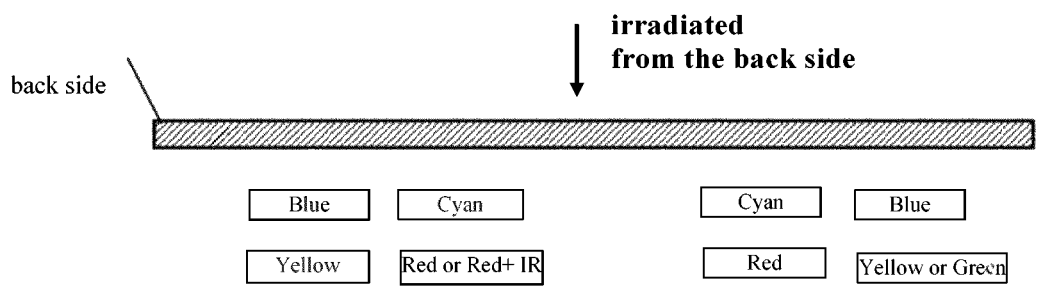

A sensing device can simultaneously have one, two, or all of the following three characteristics: double-layer or multi-layer, double-sided, and double-direction. This disclosure mainly relates to a single-sided double-layer sensing device (as shown in FIG. 22(a) and FIG. 22(b)), a double-sided double-layer sensing device (as shown in FIG. 23(a) and FIG. 23(b)), and a double-sided multi-layer sensing device (as shown in FIGS. 10-14). Irrespective of a single-sided double-layer sensing device or a double-sided double-layer sensing device or a multi-layer sensing device, all of them can be used in front side sensing (as shown in FIG. 22(a)), back side sensing (as shown in FIG. 22(b)), or double-direction sensing (as shown in FIG. 21 or FIG. 23). However, designs of the sensing devices are different under different irradiation.

A multi-spectrum photosensitive device according to an embodiment of the present disclosure comprises a base layer, wherein a plural of composite sensing pixel macro units is repeatedly arranged in accordance with a preset pattern on the base layer, the composite sensing pixel macro unit comprises at least one composite sensing pixel consisting of at least two basic sensing pixels, the basic sensing pixels are arranged in layers along a direction of light irradiation, each layer having one basic sensing pixel, and the basic sensing pixels are distributed at the top side, or bottom side, or top side and bottom side of the base layer in a manner of single side with at most two layers. It is noted that, herein the terms "top side" and "bottom side" are just used to express the relative position of two sides of the base layers, rather than limiting the absolute physical location of the surfaces of the base layer. In the following description, to convey a similar definition, the positions with respect to the position of light source are also used to describe the terms "the obverse" (the front side) and "the reverse" (the back side) of the base layer.

Herein three terms are given: composite sensing pixel macro unit, composite sensing pixel, and basic sensing pixel. The basic sensing pixel is a sensing pixel on a layer and can not be divided. The composite sensing pixel is a combination of at least two basic sensing pixels. The basic sensing pixels in the composite sensing pixel are arranged in layers along a direction of light irradiation, and each layer is provided with one basic sensing pixel (the layer herein is called a sensing-pixel layer). As described in the aforementioned description of drawings, the basic sensing pixel can be a photo diode or a photo gate. When the basic sensing pixel is a photo diode, the composite sensing pixel is in a form of a composite sensing diode pair. Of course, it is noted that, each sensing-pixel layer in a composite sensing pixel is arranged along a direction of light irradiation (which is usually the normal direction of the sensing surface of the base layer), rather than limiting to just be arranged on a side of the base layer. Between the two opposite sides of the base layer irradiated by a light source, if taking the side closer to the light source as front side of the base layer and taking the side far away from the light source as back side of the base layer, each sensing-pixel layer in a composite sensing pixel can be arranged on front side of the base layer, or on back side of the base layer, or on both front side and back side of the base layer, but there are at most two layers of sensing pixels on each side. The relationship between the arrangement and quantity of the sensing-pixel layers can be summarized that, for a direction of a light source, the arrangement of the sensing-pixel layer may be [2,0], [0,2] (i.e., single-sided double-layer), or [1,1] (i.e., double-sided double-layer), or [1,2], [2,1] (i.e., double-sided multi-layer), wherein the first number in an array is the number of sensing-pixel layers arranged on front side of the base layer in the composite sensing pixel, and the second number is the number of the sensing-pixel layer arranged on back side of the base layer in the composite sensing pixel. The composite sensing pixel macro unit, also known as a macro-pixel, is a collection of the minimum number of composite sensing pixels, from which color reconstruction can be performed. A composite sensing pixel macro unit is repeatedly arranged in accordance with a preset pattern (such as square or honeycomb pattern, or repeated ordering), so that the color can be reconstructed throughout the image plane. For the double-layer multi-spectrum sensing device, the composite sensing pixel macro unit usually comprises at least two composite pixels. However, for a two-sided multi-layer multi-spectrum sensing device, the composite sensing pixel macro unit may be one composite pixel.

Since a composite pixel may be in various types, and a plurality of composite sensing pixels arranged on the base layer may be of different types, the sensing device according to the present disclosure may have a variety of flexible forms. For a composite sensing pixel, according to the number and distribution of the basic sensing pixel therein, the composite sensing pixel may be a single-sided double-layer composite sensing pixel, a double-sided double-layer composite sensing pixel, and a double-sided multi-layer composite sensing pixel. As mentioned above, in a single-sided double-layer composite sensing pixel or a double-sided double-layer composite sensing pixel, there are two basic sensing pixels, but the distribution therein are different. The basic sensing pixels in a single-sided double-layer composite sensing pixel are arranged in layers on one side of the base layer, while the basic sensing pixels of a double-sided double-layer composite sensing pixel are arranged on two sides of the base layer. For a double-sided multi-layer composite sensing pixel, there are three or four basic sensing pixels. Since at most two sensing-pixel layers are arranged on one side of the base layer, the basic sensing pixels therein must be arranged on two sides of the base layer, at least one side is provided with two basic sensing pixels arranged in layers. It is noted that, in a special case, the composite sensing pixel may comprise a blank pixel, in other words, the pixel is used for sensing blank color. In that case, if a basic sensing pixel in a single-sided double-layer composite sensing pixel is a blank pixel, the single-sided double-layer composite sensing pixel is equivalent to a single-sided single-layer composite sensing pixel from the perspective of sensing effectiveness.

Due to the various types, the arrangement of pixels in a composite sensing pixel is quite flexible. For example, if a single-sided double-layer composite sensing pixel is arranged at a certain position on the base layer, a double-sided double-layer composite sensing pixel may be arranged at a position adjacent to the said certain position, and the double-sided multi-layer composite sensing pixels may be arranged at another position adjacent to the said certain position. In short, different types of composite sensing pixels can be arranged at different positions on the base layer. In particular, according to this feature, when all the composite sensing pixels on the base layer in a sensing device are of the identical type, the sensing device is defined according to the type of the composite sensing pixels. For example, when all the composite sensing pixels of the base layer are the single-sided double-layer composite sensing pixels, the corresponding sensing device is regarded as a single-sided double-layer sensing device, and the sensing devices adopting the other two afore-mentioned composite sensing pixels are regarded as a double-sided double-layer sensing device or a double-sided multi-layer sensing device, respectively. It is noted that, as mentioned above, the composite sensing pixel may contain a blank pixel, thus the composite sensing pixel at a position of the base layer may be degenerated. For example, in a single-sided double-layer sensing device, if a composite sensing pixel comprises one blank pixel, the single-sided double-layer sensing pixel is actually degenerated as a single-sided single-layer sensing pixel, so that from the viewpoint of the details, a composite sensing pixel of a single-sided double-layer sensing device is not entirely a single-sided double-layer sensing pixel, but in a whole, this sensing device is still classified as a single-sided double-layer sensing device. Particularly, this sensing device can also be referred to as a mixed single-sided double-layer sensing device. Correspondingly, there exist also a mixed double-sided double-layer sensing device and a mixed double-sided multi-layer sensing device.

The basic sensing pixels of a composite sensing pixel are generally arranged to sense different spectral bands of visible light or visible and infrared light. For example, one of two spectral bands of visible light or visible and infrared light orthogonal to each other can be sensed respectively by two basic sensing pixel of the composite sensing pixel. Different spectral bands may be sensed respectively by the basic sensing pixels of the composite sensing pixel and composite sensing pixels of the composite sensing pixel macro unit, thus the combination of all spectra sensed by all composite sensing pixels of a composite sensing pixel macro unit contains the spectrum indispensable for color reconstruction within the color space of RGB or CMYK.

The spectra sensed by the basic sensing pixels closest to the light source in a composite sensing pixel includes blank color, blue, green, cyan, white, and white plus infrared. The spectra sensed by the basic sensing pixels farthest away from the light source in the composite sensing pixels includes blank color, green, red, yellow, white, red plus infrared, yellow plus infrared, and white plus infrared.

Hereto the arrangement of the sensing pixel according to the present disclosure has been described. Hereinafter, the processing implementation of a multi-spectrum sensing device according to the present disclosure will be described.

Figure 5:
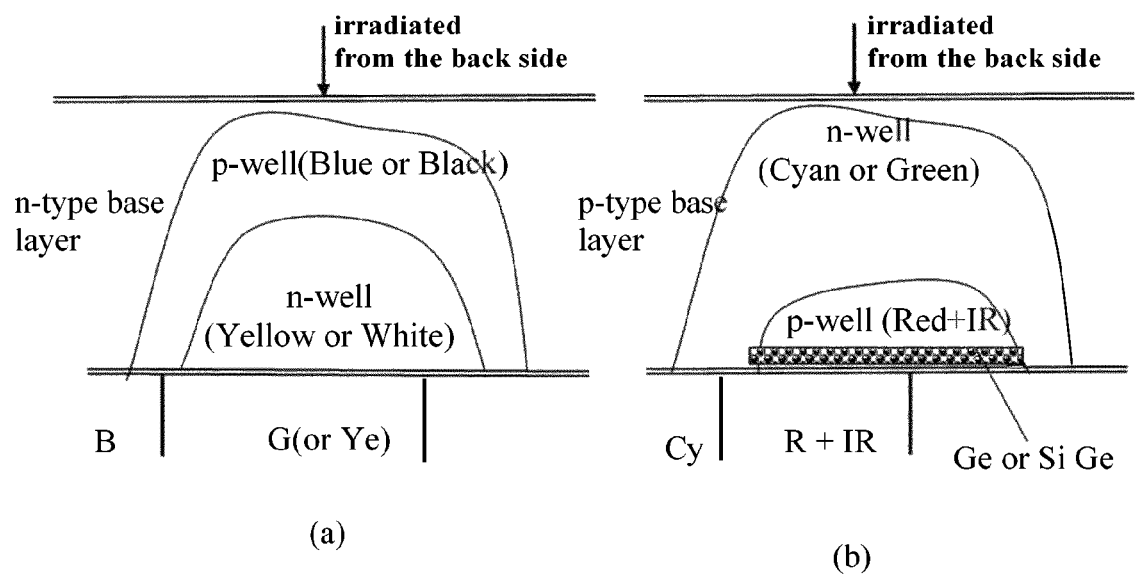
Figure 6:
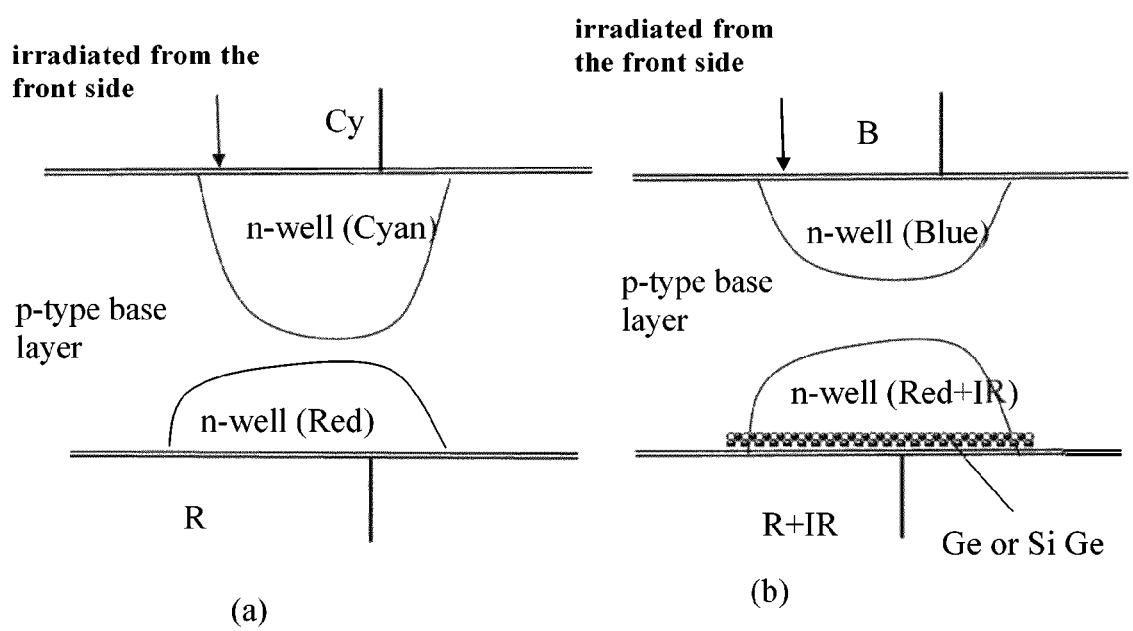
Figure 7:
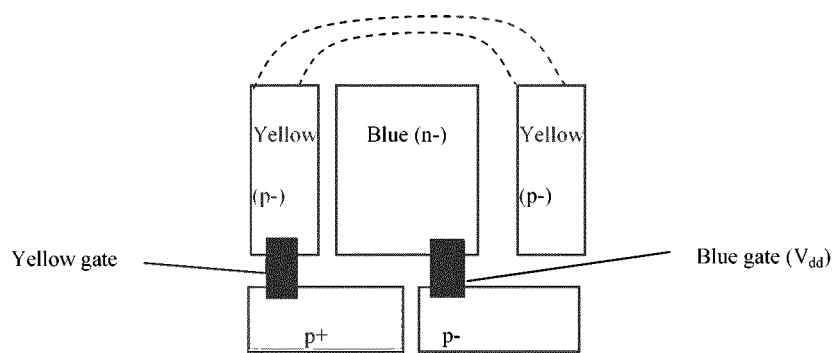
Figure 8:
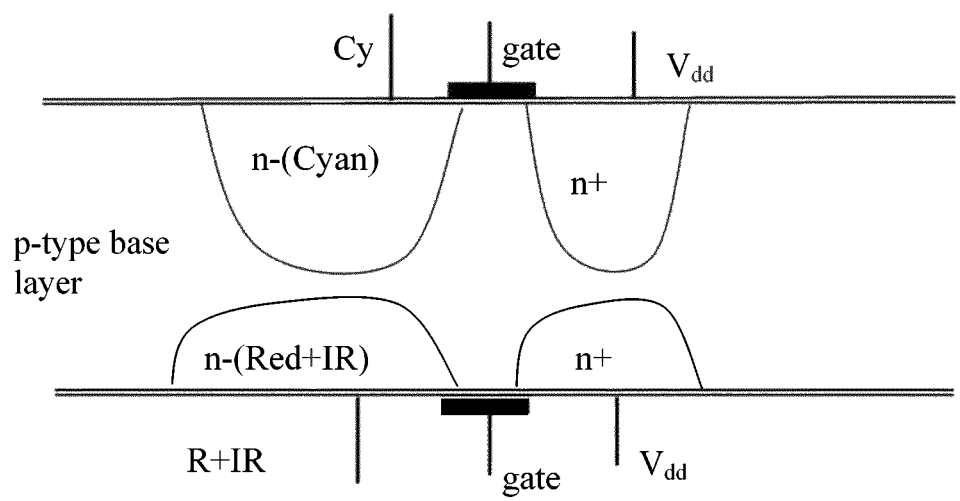

According to different materials of the base layer, an approach for achieving a single-sided double-layer multi-spectrum sensing device comprises:

Providing a base layer of N-type silicon crystal (see FIG. 5 (a)), i.e. N-Substrate, at a location of a pixel on a side of the N-type base layer, P-type impurity is doped into the base layer at a certain depth from the surface of the location into the interior of the base layer according to the requirement of color depth, so as to form a P-doped layer. The P-doped layer is a sensing layer of a composite sensing pixel, that is, it forms a basic sensing pixel of the composite sensing pixel. Then, an N-type impurity is doped into the P-doped layer at another depth, which forms an N-doped layer within the P-doped layer, that is, it forms another basic sensing pixel in the composite sensing pixel. In the case, this single-sided double-layer composite sensing pixel is formed by a composite P-N-P junction.

Another approach is to provide a base layer of P-type silicon crystal (see FIG. 5 (b)), i.e., P-substrate, at a location of a pixel on a side of the P-type base layer, N-type impurity is doped into the base layer at a certain depth from the surface of the location into the interior of the base layer according to the requirement of color depth, so as to form a N-doped layer. The N-doped layer is a sensing layer of a composite sensing pixel, that is, it forms a basic sensing pixel of the composite sensing pixel. Then, a P-type impurity is doped into the N-doped layer at another depth, which forms a P-doped layer within the N-doped layer, that is, it forms another basic sensing pixel in the composite sensing pixel. In this case, this single-sided double-layer composite sensing pixel is formed by a composite N-P-N junction.

The production of a composite sensing pixel is described above. For the production of other composite sensing pixels on the sensing side of the base layer, the processing thereof is the same. But the depths doped by impurities are different at different locations of pixels according to the wavelength of color spectrum desired to be sensed by the corresponding pixel.

Figure 1:
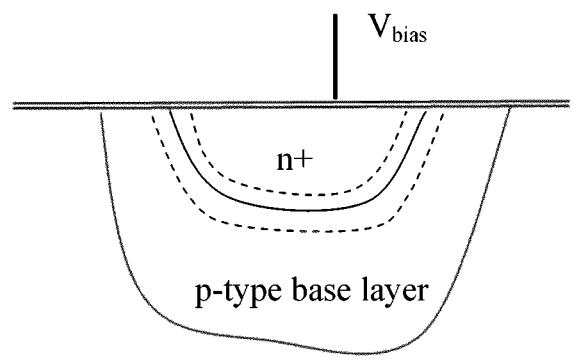
Figure 2:
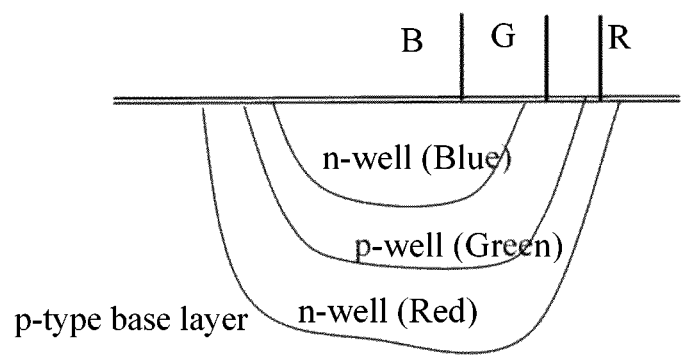
Figure 3:
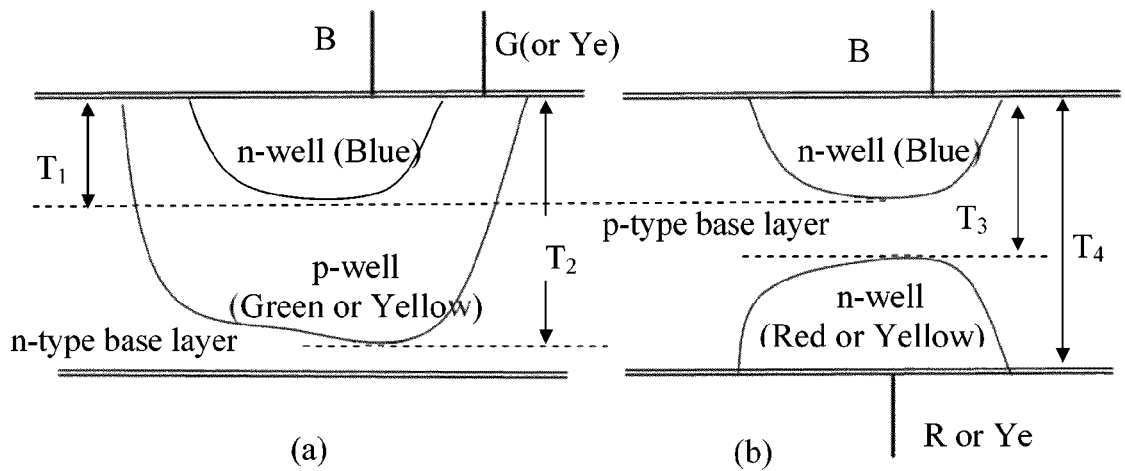
Figure 4:
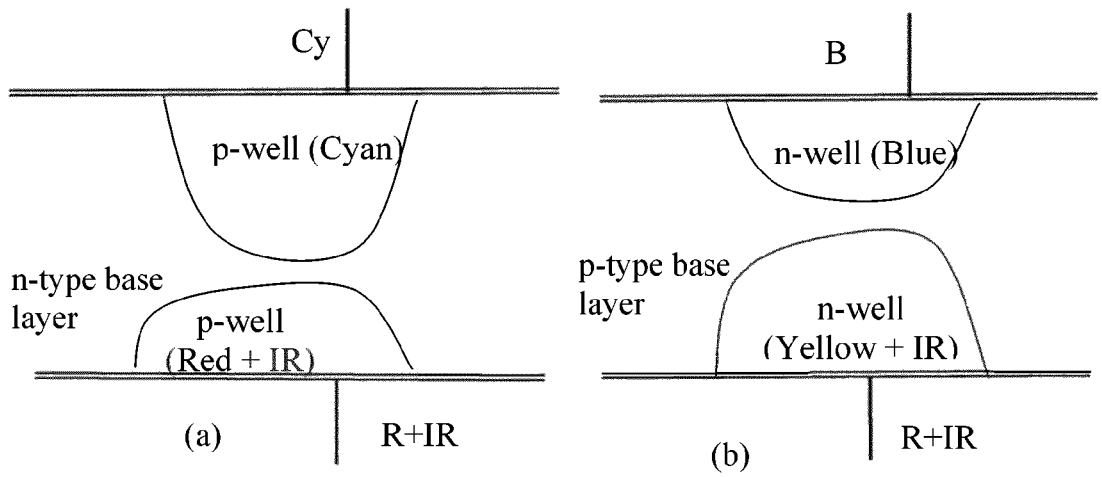

An implementation of a double-sided double-layer multi-spectrum sensing device comprises:

providing a base layer of N-type silicon crystal (see FIG. 4 (a)), i.e., N-substrate, classifying the pixels on the front side of the base layer according to the desired color, and doping P impurity with a certain depth according to the requirement of color depth for each type of pixel. Similarly, the pixels on the back side will also be classified according to the desired color, and P impurity with a certain depth is doped according to the requirement of color depth for each type of pixel. The depth of the P impurity doped is determined according to the wavelength of spectrum desired to be sensed.

Another more advantageous approach is to provide a P-type base layer of silicon crystal (see FIG. 4 (b)), i.e., P-substrate, classify the pixels on the front side according to the desired color, and dope N impurity with a certain depth according to the requirement of color depth for each type of pixel. Similarly, the pixels on the back side will also be classified according to the desired color, and N impurity with a certain depth is doped according to the requirement of color depth for each type of pixel. The depth of the N impurity doped is determined according to the wavelength of spectrum desired to be sensed. Since the mobility of N-type is better than that of P-type, the double-sided double-layer composite sensing pixel formed by this N-P-N composite junction is superior to the double-sided double-layer composite sensing pixel formed by the afore-described P-N-P composite junction.

An implementation of a double-sided multi-layer multi-spectrum sensing device comprises:

providing a base layer of N-type or P-type silicon crystal (FIG. 9-14), making the front side of the base layer as one or two sensing pixel layers in the manner of single-sided double-layer or single-sided, and making the back side as one or two sensing pixel layers in the manner of single-sided double-layer or single-sided. According to the differences between the arrangement of the front side and the back side, a composite junction of a double-sided multi-layer composite sensing pixel comprising N-P-N, P-N-P, N-P-N-P, P-N-P-N, N-P-N-P-N, P-N-P-N-P and the like is formed.

After obtaining the composite sensing pixel, if it is needed to read the optical signal, a reading circuit and other control circuits are needed. The arrangement of the reading circuit and other control circuits is designed in accordance with passive pixel or active pixel. If it is designed with active pixel, in addition to the photo diode in FIG. 3 (a), there will be a reading circuit shown in FIG. 7, and many standard timing and control circuits (not shown in figures).

For the sensing pixel layer used to sense infrared light, germanium or silicon germanium crystal layer may grow on the bottom side of the corresponding position of the sensing pixel layer, that is the bottom side of the sensing pixel layer used to sensing the infrared light, in order to improve the absorption efficiency of the infrared spectrum. In addition, after growing the germanium or silicon germanium crystal layer, a mirror reflection film formed by aluminum, silver or other materials is plated on the bottom of the basic sensing pixel, in order to reflect the unabsorbed infrared photons, which are re-absorbed by infrared sensing pixel layer. The reflected intensity is determined according to the thickness and the absorption rate of the infrared sensing pixel layer, so as to avoid unnecessary interference with other pixels.

If the multi-spectrum sensing device is used for double-direction sensing, and the direction-selected-by-pixel pattern and the direction-selected-by-area-division pattern described in the patent application titled "Multi-spectrum sensing devices and manufacturing methods thereof" (China Application No. 200810217270.2, i.e., PCT/CN2010/073441) are used, a shading film is coated on some types of pixels or pixel areas of the front side, and on the other types of pixels or pixel areas of the back side.

In the above-mentioned implementation, we can completely use photo gate to replace photo diode, resulting in obtaining a single-sided double-layer sensing device, a double-sided double-layer sensing device, and a double-sided multi-layer sensing device, which are based on the photo gate.

Since the single-sided double-layer sensing device, the double-sided double-layer sensing device, and the double-sided multi-layer sensing device according to the present disclosure provide redundant color information, for the application to which the cost and size are critical (such as mobile phone), some composite pixels may contain blank pixel, resulting in a mixed single-sided double-layer sensing device, a mixed double-sided double-layer sensing device, and a mixed double-sided multi-layer sensing device.

The present disclosure can be produced by both CCD technology and CMOS technology. Since the production of the disclosure may be ultra-high sensitivity, the basic pixel can be read by means of passive pixel, or by means of active pixel. These features make the present disclosure integrated fully with the existing mature semiconductor chip production technology, therefore, the methods or production according to the present disclosure can be widely used. The disclosure dramatically improves the performance and functionality of sensing chip, at the same time, due to the increased product yields, the cost can be reduced or at least not increased.

By means of arranging optimally the basic sensing pixel in the composite sensing pixel on two depths, and forming various types of the sensing devices, such as single-sided double-layer, double-sided double-layer, and double-sided multi-layer, the present disclosure greatly extends the types of sensing chips, and physically realizes overlap and integration of the infrared sensing and the color sensing on a single chip for the first time.

In accordance with production methods provided by the present disclosure and natural and minor modifications thereof (such as, adding a filter film), a double-layer or multi-layer composite sensing pixel, which can sense spectrum orthogonal to each other within the space of visible light or visible plus infrared light, such as (blank color, white), (blue, yellow), (blue, green), (green, red), (blue, red), (blue, red+infrared), (blue, yellow+IR), (blank color, white+IR), (white+IR), (blue/green/red/green/yellow/white, infrared) and the like, can be achieved in the form of single-sided double-layer, double-sided double-layer, or double-sided multi-layer.

By using the aforementioned sensing methods such as double-sided, double-direction, double-layer and multi-layer methods, according to the present disclosure, a single sensing device can be used in a double-direction system, for greatly reducing system cost, lowering the size, reducing system complexity, and making it possible for some applications to receive multi-spectrum or multi-direction (or multi-spectrum signals from two directions) in the same system. For example, a capsule-style camera currently used for checking the patient's gastrointestinal system has a camera mounted on just one side thereof. In order to obtain the image of a certain location in the gastrointestinal system, multiple uses may be required, which cause great pain to the patient and the big expenses. For this purpose, it is desired to improve the capture range of a single shot. And if it is necessary to mount a camera on the other side of the capsule-style camera, by using the existing technology, two systems must be mounted in a very small space, which is quite difficult. However, by using the present invention, it just needs to add a lens on the other side, and still only one sensing chip is utilized, leading to smaller space demand and lower economic cost than those of two sets of sensing systems. In addition, the present disclosure can be used to monitor both front and back direction in a monitoring camera. For many 3G mobile phones with both front camera and back camera, the front camera and back camera can be replaced by a bidirectional camera according to the present disclosure, and switching between front sense and back scene can be achieved by electronic or mechanical switches. For some surveillance system of top class hotels, if it is required to monitor scenes at both ends of the corridor, by using the present disclosure, it just needs one monitoring system to complete the necessary monitoring rather than two monitoring systems for monitoring in both directions.

According to the integration method provided by the present disclosure, color and infrared can be sensed simultaneously in the same device (using CMOS or CCD semiconductor), and color image and infrared image are overlaid in the same space position. This new type of sensing device greatly extends the dynamic range of sensing device, so as to meet the high performance of automotive, security and other fields. Moreover, it will also be used for a small-size color sensing device such as the camera of mobile phones, to significantly improve image quality.

Although the present disclosure is disclosed through the above-mentioned preferred embodiments, such disclosure should not be considered limitations to the disclosure. For those skilled in the image sensing devices (such as semiconductor image sensor chips), from the disclosure, it is possible to anticipate many variations and extensions of the present disclosure, without departing from the spirit and concept of the invention.

The invention claimed is:

1. A multi-spectrum photosensitive device, comprising a base layer, wherein a plurality of composite sensing pixel macro units is repeatedly arranged in accordance with a preset pattern on the base layer, the composite sensing pixel macro unit comprises at least one composite sensing pixel comprising at least two basic sensing pixels, the basic sensing pixels in a same composite sensing pixel are arranged in layers along a direction of light irradiation, each layer having one basic sensing pixel, wherein the composite sensing pixel includes two basic sensing pixels which are disposed respectively at the top side and bottom side of the base layer to form a double-sided double-layer composite sensing pixel.

2. The multi-spectrum photosensitive device according to claim 1, wherein the double-sided double-layer composite sensing pixel is formed by a composite P-N-P junction which is formed by doping P-type impurity on both top side and bottom side of a base layer of N-type silicon; or the double-sided double-layer composite sensing pixel is formed by a composite N-P-N junction which is obtained by doping N-type impurity on both top side and bottom side of a base layer of P-type silicon.

3. The multi-spectrum photosensitive device according to claim 1, wherein the spectral bands sensed by the basic sensing pixels in a same composite sensing pixels respectively are orthogonal to each other, the spectral bands contains spectra of visible light or visible and infrared light, the combination of spectra sensed by all the composite sensing pixels in the composite sensing pixels macro units contains spectral information indispensable for color reconstruction within the color space of RGB or CMYK.

4. The multi-spectrum photosensitive device according to claim 3, wherein the spectrum sensed by the basic sensing pixels of the composite sensing pixels closest to a light source which emits the light irradiation includes blank color, blue, green, cyan, white, and white plus infrared.

5. The multi-spectrum photosensitive device according to claim 3, wherein the spectrum sensed by the basic sensing pixels of the composite sensing pixels farthest away from a light source which emits the light irradiation includes blank color, green, red, yellow, white, red plus infrared, yellow plus infrared, and white plus infrared.

6. The multi-spectrum photosensitive device according to claim 1, wherein the bottom surface of the basic sensing pixel sensing infrared light in the bottom layer of the composite sensing pixel units grows with silicon germanium crystal layer or germanium crystal layer.

7. The multi-spectrum photosensitive device according to claim 6, wherein the bottom of the basic sensing pixels for sensing infrared light is coated with a mirror reflection film.

8. The multi-spectrum photosensitive device according to claim 1, wherein the composite sensing pixel is sampled in an active manner to form an active pixel; or the composite sensing pixel is sampled in a passive manner to form a passive pixel.

9. The multi-spectrum photosensitive device according to claim 1, wherein the basic sensing pixel in the composite sensing pixels is a photo diode or a photo gate.

10. The multi-spectrum photosensitive device according to claim 1, wherein the sensing mode of the multi-spectrum sensing device comprises front side sensing, back side sensing, or double-direction sensing mode, wherein the double-direction sensing mode includes direction—selected-by-time-sharing mode, direction—selected-by-area-division mode, or direction—selected-by-pixel mode.

11. The multi-spectrum photosensitive device according to claim 1, wherein the preset pattern includes repeated ordering, rectangular pattern, or honeycomb pattern adopted by the composite pixels.

12. A multi-spectrum photosensitive device, wherein a plurality of composite sensing pixel macro units is repeatedly arranged in accordance with a preset pattern on the base layer, the composite sensing pixel macro unit comprises at least one composite sensing pixel comprising at least two basic sensing pixels, the basic sensing pixels in a same composite sensing pixel are arranged in layers along a direction of light irradiation, each layer having one basic sensing pixel, wherein the composite sensing pixel includes two basic sensing pixels which are arranged in two layers at the top side or bottom side of the base layer to form a single-sided double-layer composite sensing pixel, wherein the bottom surface of the basic sensing pixel sensing infrared light in the bottom layer of the composite sensing pixel units grows with silicon germanium crystal layer or germanium crystal layer.

13. The multi-spectrum photosensitive device according to claim 12, wherein the single-sided double-layer composite sensing pixel is formed by a composite N-P-N junction which is formed by doping P-type impurity on a base layer of an N-type silicon to make a P-doped layer, then doping N-type impurity on P-doped layer; or the single-sided double-layer composite sensing pixel is formed by a composite P-N-P junction which is formed by doping N-type impurity on a base layer of P-type silicon to make an N-doped layer, then doping P-type impurity on the N-doped layer.

14. The multi-spectrum photosensitive device according to claim 12, wherein the spectral bands sensed by the basic sensing pixels in a same composite sensing pixels respectively are orthogonal to each other, the spectral bands contains spectra of visible light or visible and infrared light, the combination of spectra sensed by all the composite sensing pixels in the composite sensing pixels macro units contains spectral information indispensable for color reconstruction within the color space of RGB or CMYK.

15. The multi-spectrum photosensitive device according to claim 12, wherein the bottom of the basic sensing pixels for sensing infrared light is coated with a mirror reflection film.

16. The multi-spectrum photosensitive device according to claim 12, wherein the sensing mode of the multi-spectrum sensing device comprises front side sensing, back side sensing, or double-direction sensing mode, wherein the double-direction sensing mode includes direction—selected-by-time-sharing mode, direction—selected-by-area-division mode, or direction—selected-by-pixel mode.

17. The multi-spectrum photosensitive device according to claim 12, wherein the preset pattern includes repeated ordering, rectangular pattern, or honeycomb pattern adopted by the composite pixels.

18. A multi-spectrum photosensitive device, wherein a plurality of composite sensing pixel macro units is repeatedly arranged in accordance with a preset pattern on the base layer, the composite sensing pixel macro unit comprises at least one composite sensing pixel comprising at least two basic sensing pixels, the basic sensing pixels in a same composite sensing pixel are arranged in layers along a direction of light irradiation, each layer having one basic sensing pixel, wherein the composite sensing pixel includes three or four basic sensing pixels, two of which are disposed in two layers at top side or bottom side of the base layer, and the remaining basic sensing pixel(s) are disposed in one or two layers at bottom side or top side of the base layer, so as to form a double-sided multi-layer composite sensing pixel.

19. The multi-spectrum photosensitive device according to claim 18, wherein the double-sided multi-layer composite sensing pixel is formed by a composite junction of P-N-P, or N-P-N-P, or P-N-P-N, or N-P-N-P-N, wherein the composite junction is made by doping P-type impurity on both top side and bottom side of a base layer of N-type silicon to make a P-doped layer, then doping N-type impurity on the P-doped layer; or the double-sided multi-layer composite sensing pixel is formed by a composite junction of N-P-N, or N-P-N-P, or P-N-P-N, or P-N-P-N-P, wherein the composite junction is made by doping N-type impurity on both top side and bottom side of a base layer of P-type silicon to make an N-doped layer, then doping P-type impurity on the N-doped layer.

20. The multi-spectrum photosensitive device according to claim 18, wherein the bottom surface of the basic sensing pixel sensing infrared light in the bottom layer of the composite sensing pixel units grows with silicon germanium crystal layer or germanium crystal layer.

21. The multi-spectrum photosensitive device according to claim 20, wherein the bottom of the basic sensing pixels for sensing infrared light is coated with a mirror reflection film.

22. The multi-spectrum photosensitive device according to claim 18, wherein the spectral bands sensed by the basic sensing pixels in a same composite sensing pixels respectively are orthogonal to each other, the spectral bands contains spectra of visible light or visible and infrared light, the combination of spectra sensed by all the composite sensing pixels in the composite sensing pixels macro units contains spectral information indispensable for color reconstruction within the color space of RGB or CMYK.

23. The multi-spectrum photosensitive device according to claim 22, wherein the spectrum sensed by the basic sensing pixels of the composite sensing pixels closest to a light source which emits the light irradiation includes blank color, blue, green, cyan, white, and white plus infrared.

24. The multi-spectrum photosensitive device according to claim 22, wherein the spectrum sensed by the basic sensing pixels of the composite sensing pixels farthest away from a light source which emits the light irradiation includes blank color, green, red, yellow, white, red plus infrared, yellow plus infrared, and white plus infrared.

25. The multi-spectrum photosensitive device according to claim 18, wherein the sensing mode of the multi-spectrum sensing device comprises front side sensing, back side sensing, or double-direction sensing mode, wherein the double-direction sensing mode includes direction—selected-by-time-sharing mode, direction—selected-by-area-division mode, or direction—selected-by-pixel mode.

26. The multi-spectrum photosensitive device according to claim 18, wherein the preset pattern includes repeated ordering, rectangular pattern, or honeycomb pattern adopted by the composite pixels.

\* \* \* \* \*